(12) United States Patent
Leschinsky et al.

(10) Patent No.: US 6,200,339 B1
(45) Date of Patent: Mar. 13, 2001

(54) ENDOVASCULAR SPLIT-TUBE BIFURCATED GRAFT PROSTHESIS AND AN IMPLANTATION METHOD FOR SUCH A PROSTHESIS

(75) Inventors: Boris Leschinsky, Waldwick, NJ (US); Dennis Goupil, Norcross, GA (US)

(73) Assignee: Datascope Investment Corp., Montvale, NJ (US)

( * ) Notice: Subject to any disclaimer, the term of this patent is extended or adjusted under 35 U.S.C. 154(b) by 0 days.

(21) Appl. No.: 09/256,026

(22) Filed: Feb. 23, 1999

(51) Int. Cl.[7] .................................................. A61F 2/06

(52) U.S. Cl. ............................................... 623/1.35

(58) Field of Search .................................. 623/1.1, 1.35, 623/1.37, 1.13; 606/153, 191, 198

(56) References Cited

U.S. PATENT DOCUMENTS 5,628,783 * 5/1997 Quiachon et al. ..................... 623/1.1
5,851,228 * 12/1998 Pinheiro .............................. 623/1.35
5,904,713 * 5/1999 Leschinsky ......................... 623/1.35

* cited by examiner

*Primary Examiner*—Michael Buiz
*Assistant Examiner*—Kevin Truong
(74) *Attorney, Agent, or Firm*—Abraham P. Ronai (57) ABSTRACT

A method and device for endoluminally bypassing blood flow through an aneurysm in the vicinity of a branched blood vessel, having a main branch, a first branch, and a second branch. The method comprises steps of: advancing a distal end of a separable guide wire into the first branch, through the main branch, and out of the second branch; disposing a split-tube bifurcated graft, having a split in the middle and a middle portion that is tapered outwardly, about the guide wire; advancing said graft into the first branch, through the main branch, and out of the second branch; disposing stents about the guide wire and within the graft; advancing said stents simultaneously into the first and second branches until said stents stop against the guide wire; moving the graft-stent-guide wire assembly towards the cephalic portion of the aneurysm; deploying the stents; and finally removing the guide wire, which has a first portion and a second portion, from the patient by first removing a locking wire disposed within the guide wire and then by pulling the first and second portions apart simultaneously.

3 Claims, 8 Drawing Sheets

ENDOVASCULAR SPLIT-TUBE BIFURCATED GRAFT PROSTHESIS AND AN IMPLANTATION METHOD FOR SUCH A PROSTHESIS

BACKGROUND OF THE INVENTION

1. Field of the Invention

The invention relates to an endovascular graft prosthesis and an implantation method for such a prosthesis. More particularly, the invention relates to an endovascular split-tube bifurcated graft prosthesis and an implantation method for such a prosthesis.

2. Description of the Prior Art

Aortic aneurysms represent a significant medical problem for the general population. Aneurysms within the aorta presently affect between two and seven percent of the general population and the rate of incidence appears to be increasing. This form of atherosclerotic vascular disease (hardening of the arteries) is characterized by a degeneration in the arterial wall in which the wall weakens and balloons outward by thinning. An abdominal aortic aneurysm is a dilation of the main artery of the body. Until the affected artery is removed or bypassed, a patient with an abdominal aortic aneurysm ("AAA") must live with the threat of aortic aneurysm rupture and death. See Brody, J. E., "Aneurysm: A Potential Killer Lurking in the Aorta," The New York Times, Apr. 13, 1994, at C14.

One known clinical approach for patients with an abdominal aortic aneurysm is a surgical repair procedure. This is an extensive operation involving transperitoneal or retroperitoneal dissection of the aorta and replacement of the aneurysm with an artificial artery known as a prosthetic graft. This procedure requires a significant abdominal incision extending from the lower border of the breast bone down to the pubic bone to expose the abdominal aorta and the aneurysm so that the graft can be directly implanted. The operation requires a general anesthesia with a breathing tube, extensive intensive care unit monitoring in the immediate post-operative period, along with blood transfusions and stomach bladder tubes. All of this imposes stress on the cardiovascular system. Also associated with this procedure are well recognized morbidity (15%) and mortality (2– 7%) rates. See Ernst, C. B. "Abdominal aortic Aneurysms," New England J. Med., Vol. 328: 1167–1172 (Apr. 22, 1993).

Today, there is the potential for a significantly less invasive clinical approach to aneurysm repair known as endovascular grafting. Parodi et al. provide one of the first clinical descriptions of this therapy. Parodi, J. C., et al., "Transfemoral Intraluminal Graft Implantation for Abdominal Aortic Aneurysms," 5 Annals of Vascular Surgery 491 (1991). Endovascular grafting involves the transluminal placement of a prosthetic arterial graft in the endoluminal position (within the lumen of the artery). By this method, the graft is attached to the internal surface of an arterial wall by means of attachment devices (expandable stents), one above the aneurysm and a second stent below the aneurysm.

Stents are devices that permit fixation of a graft to the internal surface of an arterial wall without sewing. Expansion of radially expandable stents is conventionally accomplished by dilating a balloon at the distal end of a balloon catheter. In U.S. Pat. No. 4,776,337, Palmaz describes a balloon-expandable stent which has received the greatest experimental and clinical application for endovascular treatments. Also known are self expanding stents, such as described in U.S. Pat. No. 4,655,771 to Wallsten.

Attachment of the stents above and below the aneurysm is a conceptually straightforward procedure when the aortic aneurysm is limited to the abdominal aorta and there are significant portions of normal tissue above and below the aneurysm (see FIG. 1). Unfortunately, 40–60% of aneurysms do not have suitable neck portions of normal tissue at the caudal portion (furthest from the head) of the aorta. Also, the severe tortuosity of the iliac arteries and the marked angulation of the aortoiliac junction compound the difficulty of fixing the stent in the caudal portion of the aorta. This situation is only exacerbated by the tendency of the abdominal aortic artery to elongate caudally during aneurysm formation. For want of sufficient normal aortic tissue to suitably attach a prosthetic graft at the caudal end of an aneurysm, or because of extension of the aneurysmal sac into the iliac arteries, bifurcated grafts have been developed that comprise a single body terminating with two limbs.

As a therapy to bypass an abdominal aortic aneurysm as well as any associated common iliac aneurysms, endoluminal deployment of a conventional bifurcated graft has presented significant issues to clinical operators in the field, primarily with respect to the positioning of one of the limbs of the graft in the contralateral iliac artery. The contralateral iliac artery is the artery that the conventional endoluminal bifurcated graft is not being advanced through. This procedure requires that both limbs of the graft be inserted into one branch of the femoral arterial system before being drawn or pulled over to the contralateral branch. This is to ensure that the graft is suitably positioned within the aorta and each of the right and left common iliac arteries. Even when tightly packaged, the bifurcated graft is a bulky device to advance through an often narrow single iliac artery.

The process of pulling one limb of the graft to the contralateral artery is time consuming and increases the risk of procedural complications, such as twisting and kinking of the graft-limb and injury to the vessel wall which can result in micro-embolization. As one limb of the graft is pulled across the frequently tortuous and twisted iliac artery anatomy, the graft may twist or kink. Any graft twist or kink may reduce or entirely cut-off blood flow to the arterial tree downstream thereof.

The procedure of drawing one limb of the prosthetic graft from one branch of the arterial system to the contralateral branch requires significant and skillful wire catheter manipulation within the aneurysmal cavity. See, for example, Chuter T. A. M., et al., "Transfemoral Endovascular Aortic Graft Placement," J. of Vascular Surgery 18: 185–190 (August, 1993). This procedure may result in micro-embolization of clots which are known to form within aneurysmal sacs. If these clots are disturbed or dislodged from the aortic aneurysm, they may break up into small fragments and flow downstream to other arteries. Excessive guide wire manipulation may also induce "churning" within the aneurysmal cavity which can cause proximal reflux or retrograde flow of thrombotic or embolic material into the arteries that supply circulation to the kidneys, intestines, and the liver.

Accordingly, there exists a need for a method for safely and effectively bypassing an aneurysm, such as an abdominal aortic aneurysm, located at or extending into a bifurcation in the vasculature, such as the common iliac arteries. There also exists the need for a guide wire which can be removed with minimal guide wire manipulation so as to prevent the above mentioned problem of "churning."

WO 95/16406 discloses an endovascular graft prosthesis for arrangement at or in the arterial system of a patient and comprising a substantially tubular main body for location in an upstream arteria above the bifurcation and substantially tubular legs joining said main body and extending via the bifurcation into each of two downstream branch arteries. This graft design avoids the problems inherent in forcing the entire graft through one of the narrow iliac arteries. One disadvantage of this prosthesis, however, is the complexity involved in making connections and achieving a good seal between the tubular legs and the main body.

U.S. Pat. No. 5,507,769 discloses an endoluminal bifurcated graft comprising two tubes each of which is advanced through the femoral and iliac arterial system on opposite sides of a patient's body. The distal ends of the tubes are aligned in a common region of normal aortic tissue above the aneurysm, after which "D" shaped vascular stents are deployed effectively locking the tubes in position and excluding blood from the aneurysmal cavity. One disadvantage of this prosthesis, however, is the complexity, and the resultant necessity for fluoroscopic assistance, in aligning the distal ends of each tube.

While these units may be suitable for the particular purpose employed, or for general use, they would not be as suitable for the purposes of the present invention as disclosed hereafter.

SUMMARY OF THE INVENTION

Accordingly, it is an object of the invention to produce a split-tube bifurcated endovascular graft prosthesis that can be implanted by a considerably simpler implantation operation than the above mentioned prior art solutions.

It is another object of the invention to produce a split-tube bifurcated graft prosthesis that employs a separable guide wire which minimize "churning" within the aneurysmal cavity.

The invention is a method and device for endoluminally bypassing blood flow through an aneurysm in the vicinity of a branched blood vessel, having a main branch, a first branch, and a second branch. The method comprises steps of advancing a distal end of a separable guide wire into the first branch, through the main branch, and out of the second branch; disposing a split-tube bifurcated graft, having a split in the middle and a middle portion that is tapered outwardly, about the guide wire; advancing said graft into the first branch, through the main branch, and out of the second branch; disposing stents about the guide wire and within the graft; advancing said stents simultaneously into the first and second branches until said stents stop against the guide wire; moving the graft-stent-guide wire assembly towards the cephalic portion of the aneurysm, deploying the stents; and finally removing the guide wire, which has a first portion and a second portion, from the patient by first removing a locking wire disposed within the guide wire and then by pulling the first and second portions apart simultaneously.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DEFINITIONS

The terms "distal" and "proximal" as used in this specification refer only to the catheter device itself and the stents being deployed, but not to the vasculature. The present method contemplates advancement of a catheter in a retrograde manner (against the blood flow). Therefore, as the catheter is advanced distally from, for example, the aorta, it advances to a more proximal portion of the vasculature with respect to the heart, as understood by those skilled in the art. Thus, to avoid ambiguity, the vasculature is referred to with respect to the cephalic (closer to the head) and caudal (further from the head) directions. Also, as used in this description and in the claims, the term "above", in the context of relative positioning with respect to the aneurysm, refers to the region cephalic of the aneurysm, for example, within the aorta, whereas "below" refers to the region of the vasculature caudal of the aneurysm, for example, within the common iliac arteries.

DETAILED DESCRIPTION OF THE PREFERRED EMBODIMENTS

A. PRIOR ART TECHNIQUES

Figure 1:
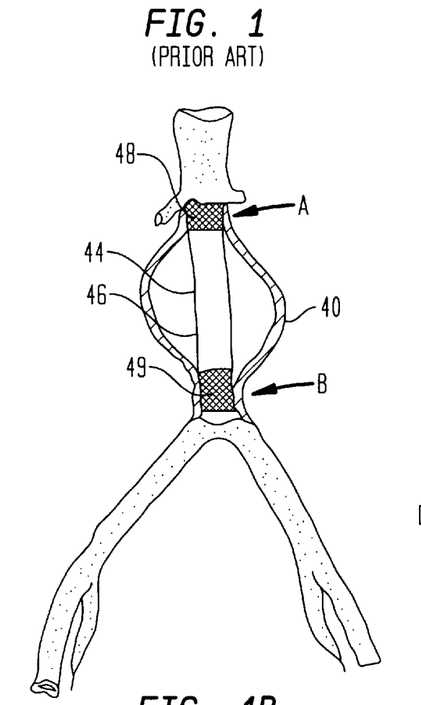
FIG. 1 is a diagrammatic view of a portion of a human vascular system depicting an abdominal aortic aneurysm which has been endoluminally bypassed in a manner previously described by Parodi et al.

In FIG. 1 there is a diagram of a vascular system that depicts, in part, the arterial system in the vicinity of the abdominal aorta. In order to use a tubular endoluminal graft 46, a sufficient length of normal artery both above and below an aortic aneurysm 40 is required so that a graftstent complex 44 can be effectively sealed or attached. The graftstent complex 44 comprises a thin-walled, crimped, knitted graft 46 of polyester, expandable polytetrafluoroethelyne (ePTFE), or similar material that overlaps and is sutured to at least a cephalic stent 48. As shown in the Figures, the graftstent complex 44 further includes a caudal stent 49, but the invention has application with a graftstent complex 44 having only one stent, e.g., the stent 48.

Figure 1A:
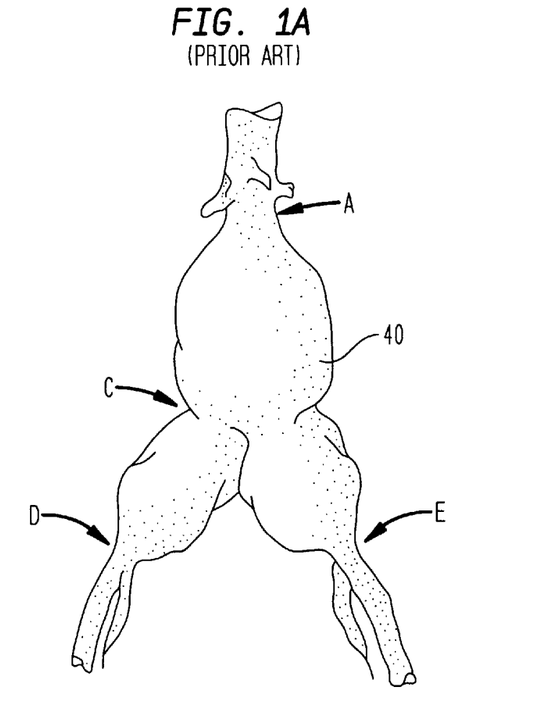
FIG. 1A is a diagrammatic view of a portion of a human vascular system depicting an abdominal aortic aneurysm and associated aneurysms of the left and right common iliac arteries.

As depicted in FIG. 1, a stent 48 anchors the tubular endoluminal graft 46 above the aneurysm at point A and another stent 49 below the aneurysm at point B. When the length of the neck is insufficient to seat a stent at point B, a bifurcated device is necessary. The anatomic arrangement that would benefit from a bifurcated device is depicted in FIG 1A. Here, there is insufficient normal artery to seat the stent 49 at point C because of the aneurysms in the associated common iliac arteries.

Figure 1B:
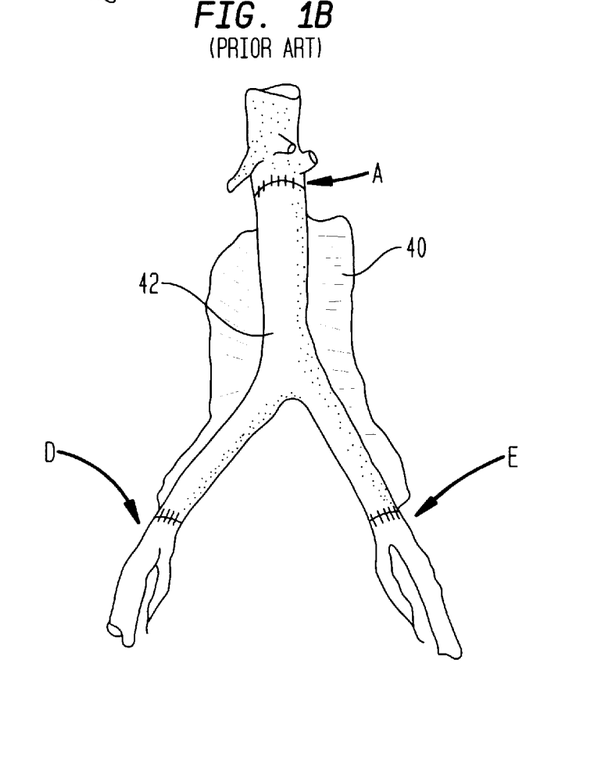
FIG. 1B is the vasculature of FIG. 1A after exclusion of the aneurysm and attachment of a graft in conventional manner.

When the anatomic constraint of FIG 1A is present, the standard vascular surgical approach requires that a bifurcated extraluminal graft procedure be performed. This procedure is performed by making a large abdominal incision from the breast-bone down to the pubic bone in the middle of the abdominal wall (not shown). The intestines are pushed aside and the aneurysm is approached directly where it sits adjacent to the spine, near the patient's back. With clamps placed above the aneurysm at point A and additional clamps placed on the iliac arteries at points D and E, blood flow is controlled so that an artificial graft 42 can be sewn into position as a new conduit to replace the diseased aorta 40, as shown in FIG 1B. This procedure involves an extensive operation and recovery period, with an intensive care unit stay and a significant period of post procedure convalescence.

It is difficult to safely endoluminally deploy a conventional bifurcated graft when the anatomic constraint of FIG 1A is present. Because both limbs are inserted and advanced through a single branch of the femoral arterial system, one of the limbs must ultimately be pulled or drawn into the contralateral or opposite branch so that the graft is suitably positioned across both the aortic aneurysm and the associated common iliac aneurysms to supply circulation to each of the lower limbs. Importantly, bifurcated grafts are frequently too bulky to advance through a single iliac artery, especially in view of the fact that the graft-limb for the contralateral branch must be inserted together with the graft-limb of the ipsilateral branch. In addition, care must be taken not to twist or kink the graft as it is placed in the contralateral artery. The caudal portion of the graft must not stretch across the mouth of the internal iliac artery which would result in inadvertent occlusion of that artery.

B. METHOD AND APPARATUS OF THE PRESENT INVENTION

Figure 2:
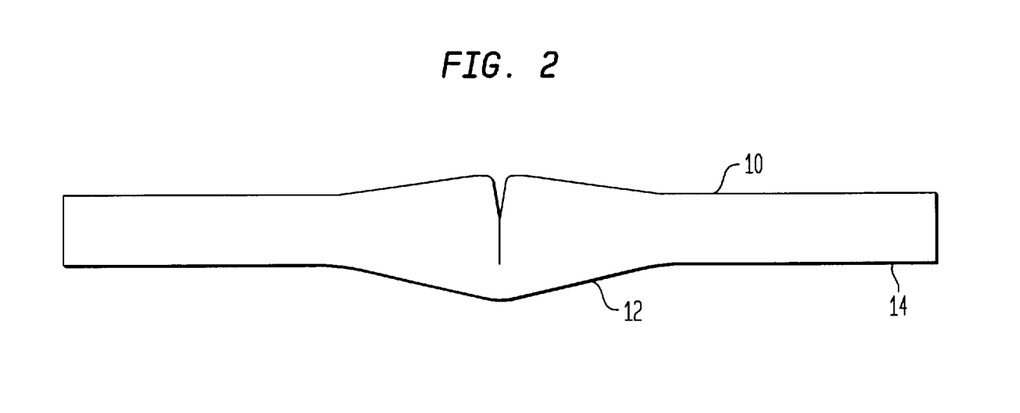
FIG. 2 illustrates a longitudinal view of a split-tube bifurcated graft.

FIG. 2 illustrates a longitudinal view of a split-tube bifurcated graft 10 having a middle portion 12 and ends 14 for use in treating abdominal aortic aneurysms. The middle portion 12 of said graft 10 is tapered outwardly to achieve a larger diameter than the ends 14. The graft 10 is partially split in the middle.

Figure 3:
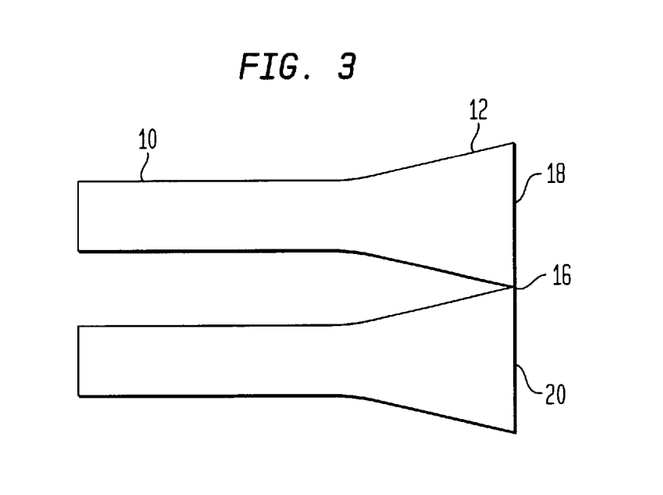
FIG. 3 illustrates the graft of FIG. 2 folded about the split in the middle of the graft.
Figure 4:
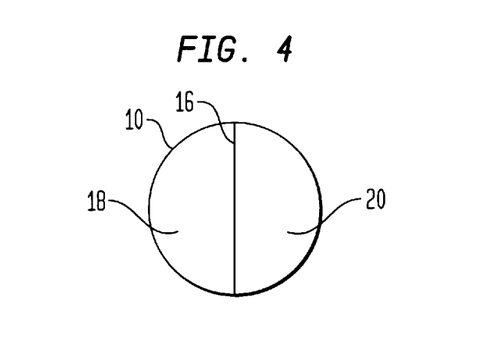
FIG. 4 illustrates a front view of the folded middle portion of the graft of FIG. 3.

FIG. 4 illustrates a frontal view of the folded middle portion 12 of the graft 10 of FIG. 3. A septum 16 forms a partition between a left lumen 18 and a right lumen 20 and transversely extends across the graft 10. In a preferred embodiment, for a given diameter of an aortic vessel, the corresponding diameter of the folded middle section 12 of the graft 10, as shown in FIG. 4, is approximately 18% smaller. Accordingly, once the branches of the graft are folded the portions of the graft immediately to the right and left of the split together form a circular passageway, with a partition in the middle, having the correct perimeter. The circular shape of the folded middle section 12 is maintained by 2 "D" shaped stents (not shown) which are inserted into the first lumen 18 and the second lumen 20.

Figure 5A:
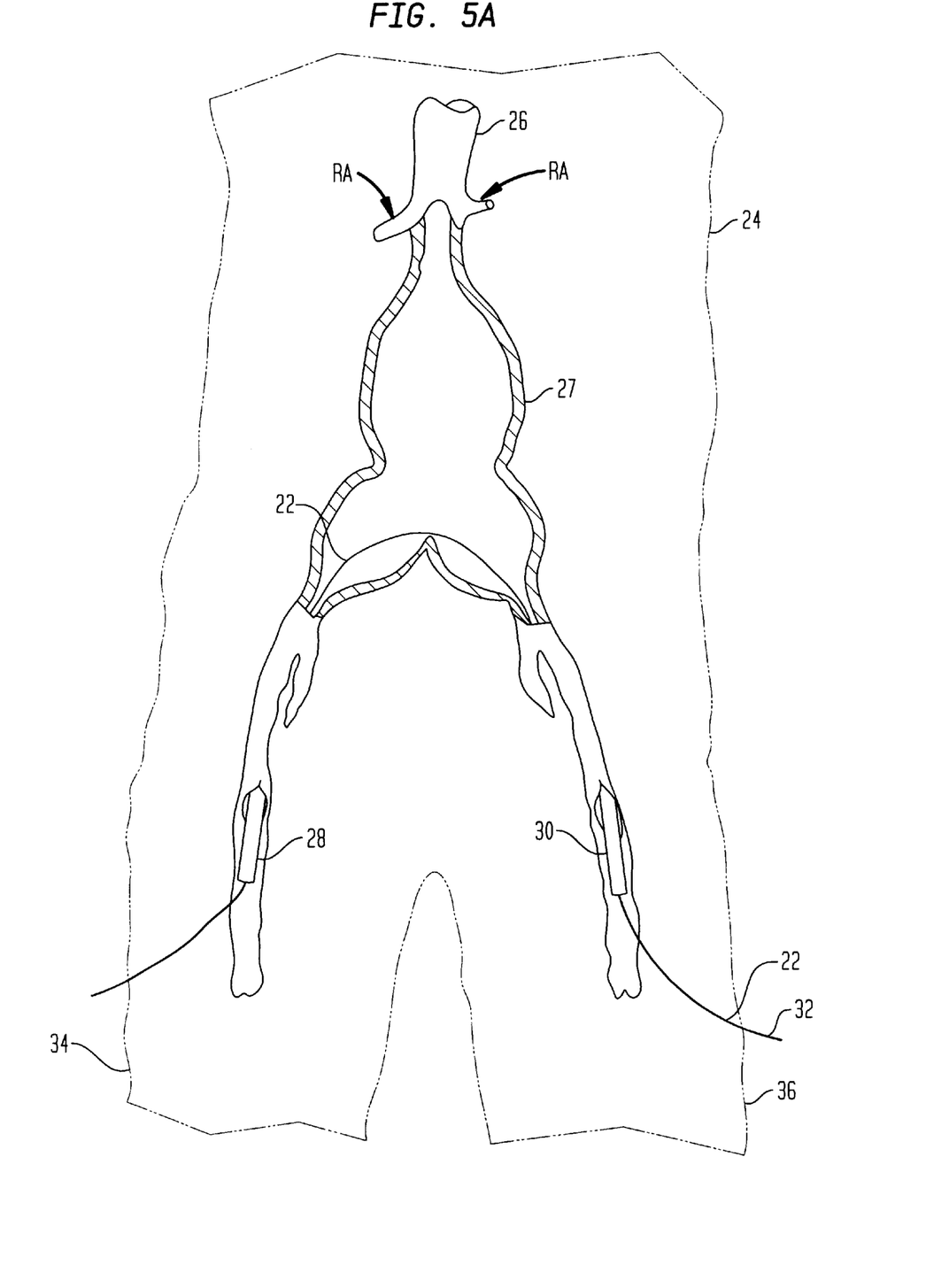
FIG. 5A illustrates the state of affairs after the first stage of graft insertion steps is completed.

FIG. 5A depicts an aneurysm 27 in the infrarenal aorta and the common iliac arteries. The infrarenal aorta is that portion of an aorta 26 disposed caudal of the left and right renal arteries, labeled RA. Because the aneurysm extends through the aortoiliac junction, no normal aortic arterial tissue at the caudal end of the aorta is present to which a caudal stent may be secured. Conventional vascular surgical therapies for this anatomical arrangement have been noted above, along with the difficulties posed to operators performing endoluminal bypass procedures using conventional bifurcated grafts.

FIG. 5A illustrates the state of affairs after the first stage of insertion steps of the graft 10 into an aorta 26 of a patient 24, having a first leg 34 and a second leg 36, is completed. A first sheath 28 is inserted into the first leg 34 of the patient 24. The second sheath 30 is inserted into the second leg 36 of the patient 24. A guide wire 22 having a distal end 32 is inserted into the first sheath 28 in an upstream direction. A snare which is inserted into the second sheath 30 in an upstream direction is used to pull the distal end 32 of the guide wire 22 out of the second sheath 30.

Figure 5B:
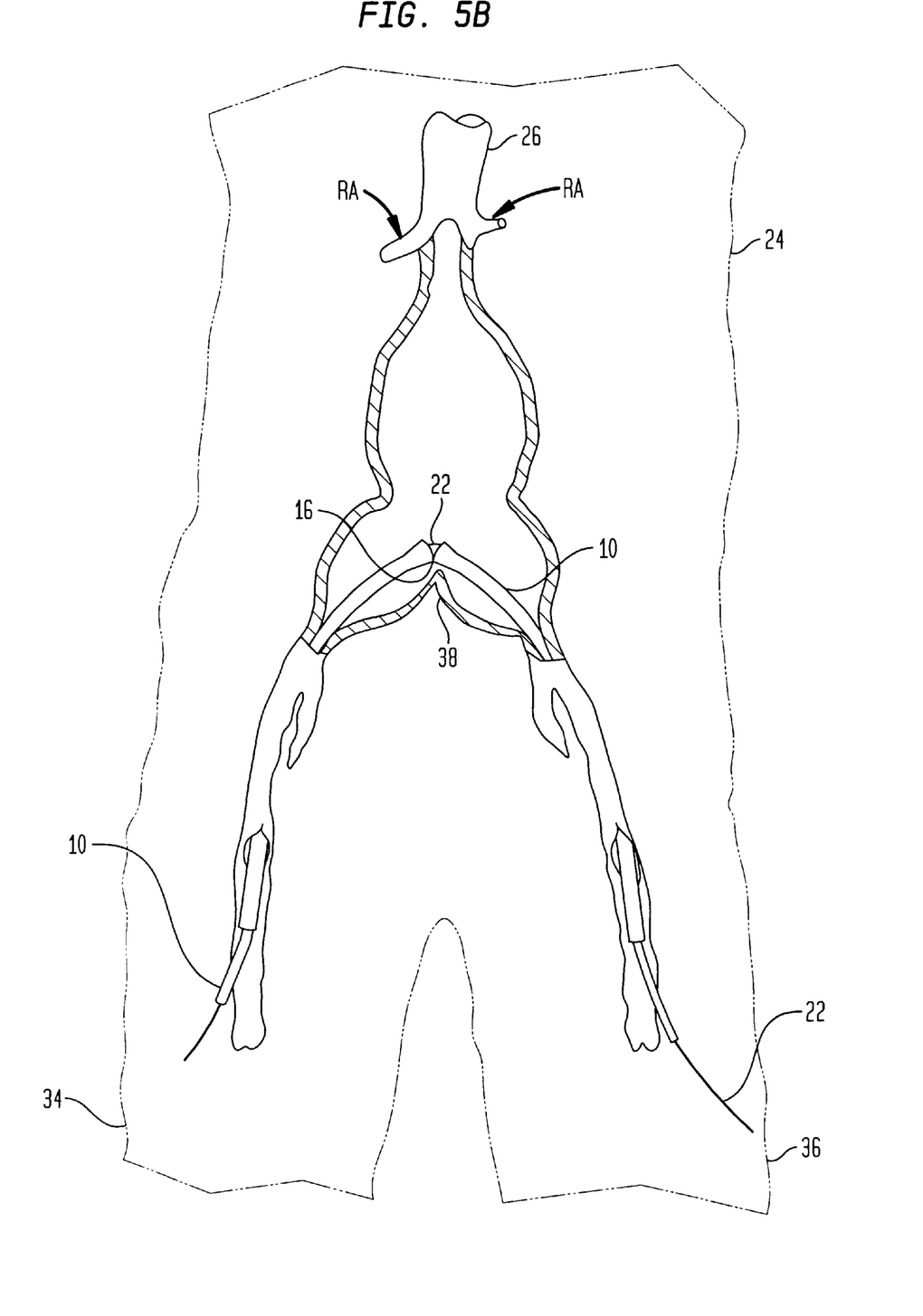
FIG. 5B illustrates the state of affairs after the second stage of graft insertion steps is completed.

FIG 5B illustrates the state of affairs after the second stage of insertion steps is completed. The second stage involves inserting the graft 10 into the aorta 26 of the patient 24 by disposing the graft 10 about the guide wire 22 and pushing the graft 10 into the aorta 26 until the septum 16 lies at a base 38 of a bifurcation of the artery 26.

Figure 5C:
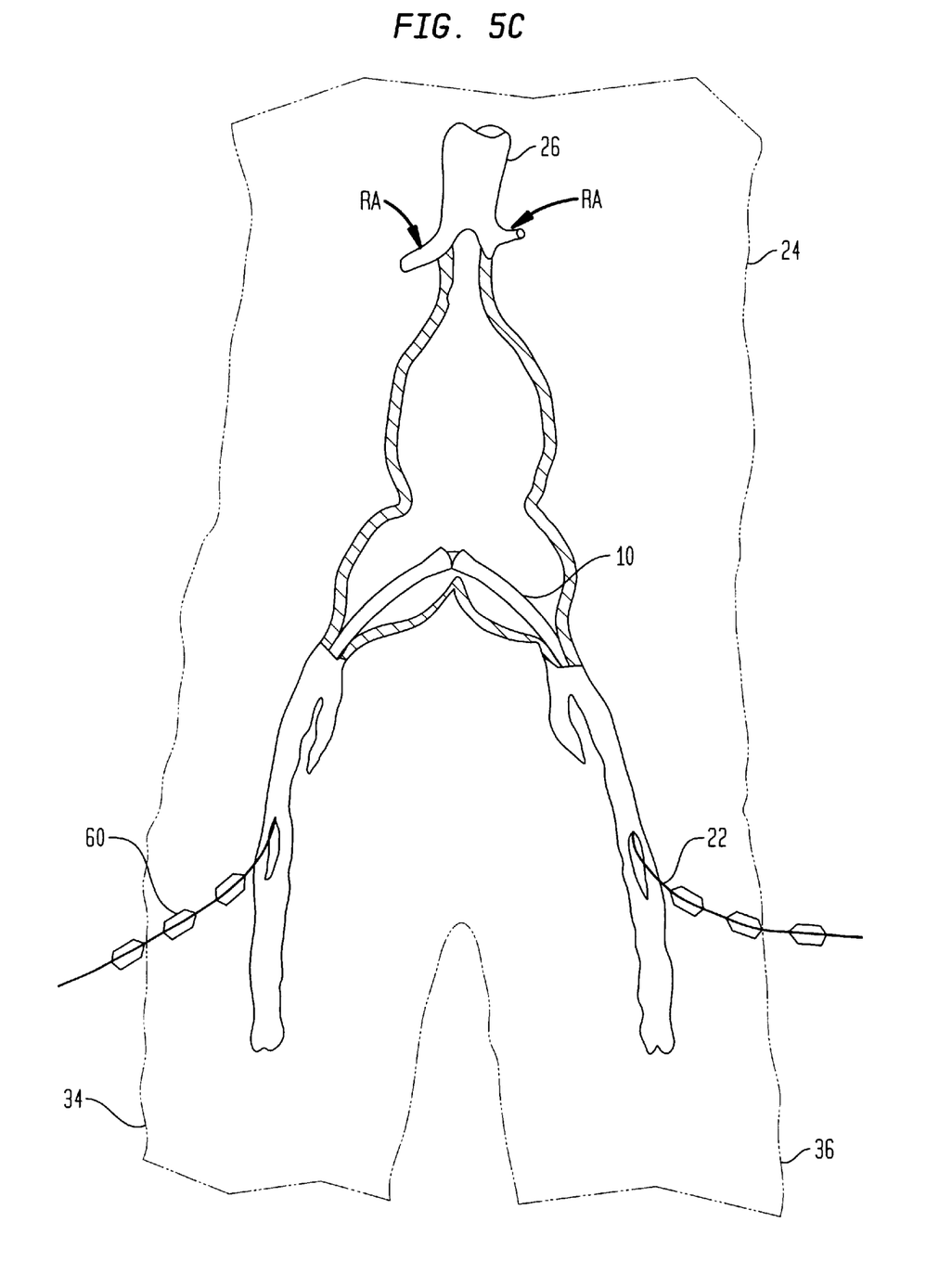
FIG. 5C illustrates the state of affairs after the third stage of graft insertion steps is completed.

FIG. 5C illustrates the state of affairs after the third stage of insertion steps is completed. The third stage involves removing both the first sheath 28 and the second sheath 30, trimming the graft 10 to size, releasing the graft 10, and inserting stents 60 into both the first leg 34 and the second leg 36 until the stents 60 stop against the guide wire 22. The stents 60 are disposed about the guide wire 22 and within the graft 10. The stents 60 are disposed within the graft 10 by simultaneously pushing the string of stents 60 into the first leg 34 and the second leg 36 in an upstream direction while firmly holding the guide wire 22 in place. As shown in FIG. 5C, after the third step the graft 10 is still in a collapsed state. In an alternate embodiment of the invention the graft 10 may be inserted into the artery 26 together with one or more supportive stents rather than being advanced into an already inserted graft.

Figure 5D:
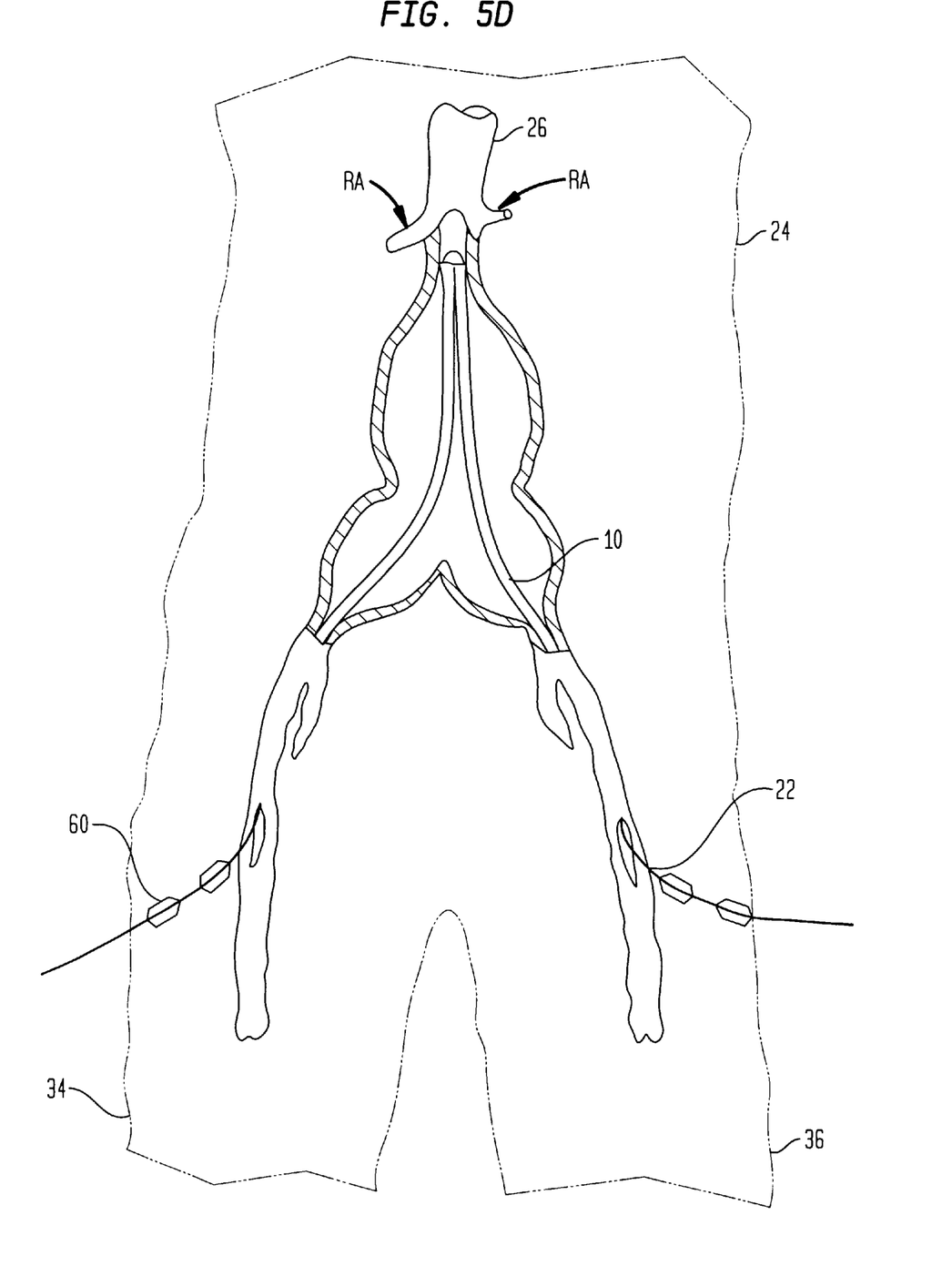
FIG. 5D illustrates the state of affairs after the graft-stent-guide wire assembly is moved into position.

FIG. 5D illustrates the state of affairs after the fourth stage of insertion steps is completed. The fourth stage involves moving the entire assembly up and positioning the septum 16 just below the renal arteries, labeled RA.

Figure 5E:
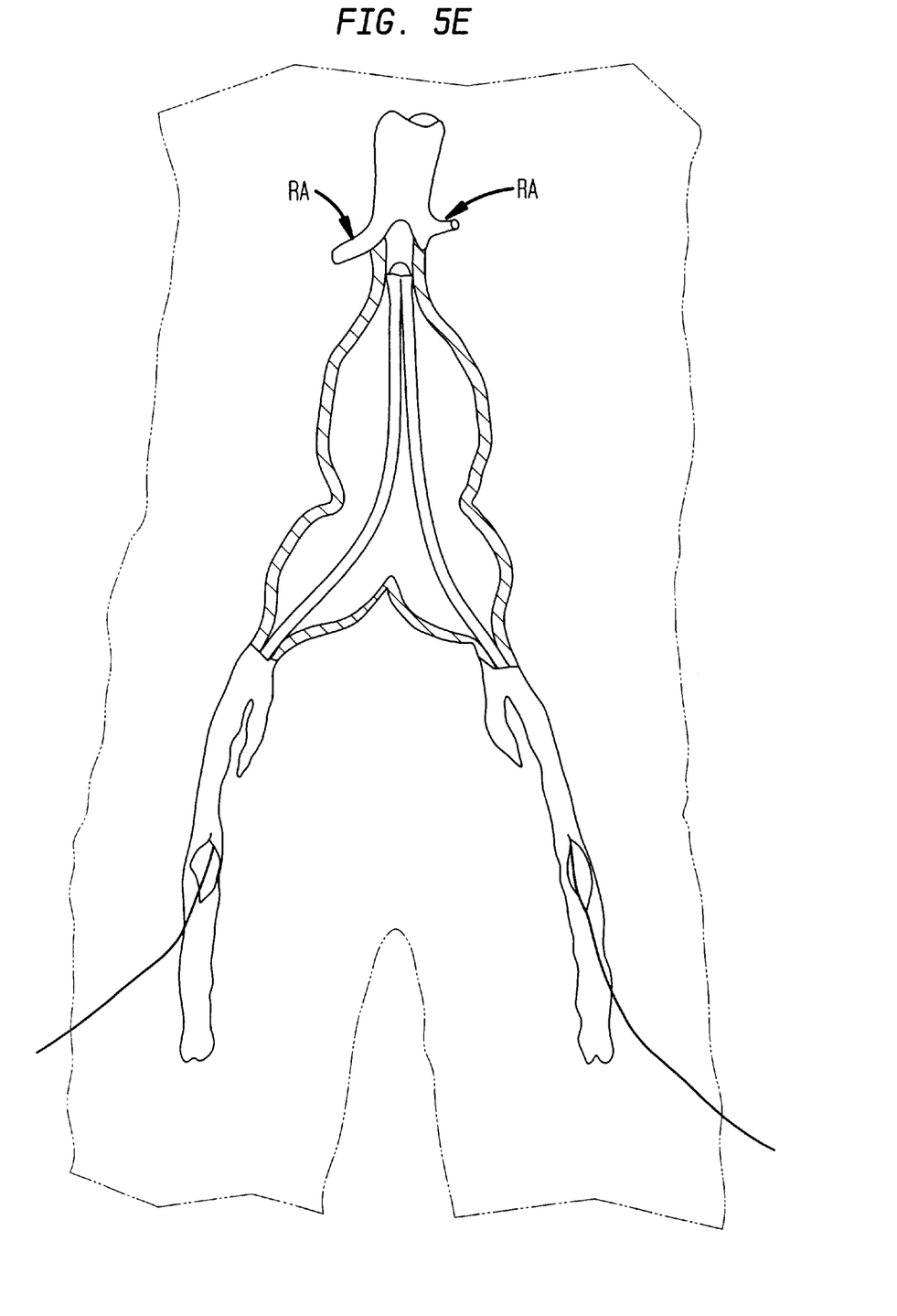
FIG. 5E illustrates the state of affairs after the stents are deployed.

FIG. 5E illustrates the state of affairs after the stents are deployed. The stents 60 used to secure the middle portion 12 of the graft to the cephalic region of the aneurysm have a "D" shape such that when the graft is in a folded state, as illustrated in FIGS. 3, 4, and 5E, the distal end of the folded graft 10 takes on a circular shape.

Figure 6:
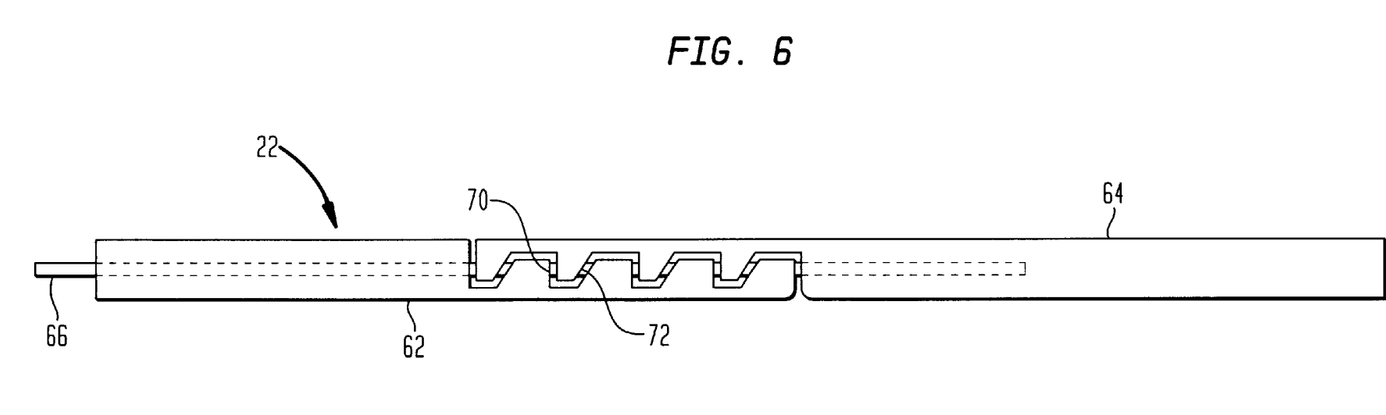
FIG. 6 illustrates a plan view of a separable guide wire.

The final insertion step involves removing the guide wire 22. FIG. 6 illustrates a longitudinal view of a preferred embodiment of the guide wire 22 which has a first portion 62, a second portion 64, and a locking wire 66. One should note, however, that use of a standard guide wire is anticipated. The distal end of the first portion 62 and the proximal end of the second portion 64 are hinged together with the locking wire 66 acting as a pin and have teeth 61 with perpendicular sides 70 and angled sides 72. The locking wire 66 is disposed within the proximal portion of the second portion 64 and the entire first portion 62 and extends beyond the proximal end of the first portion 62. The first portion 62 may be shorter in length than the second portion 64. The guide wire 22 can be removed from the graft 10 by first pulling the locking wire 66 out from inside the graft 10 and then by pulling the first portion 62 and the second portion 64 apart. The first portion 62 is removed from the first leg 34 and the second portion 64 is removed from the second leg 36. A separable guide wire as herein disclosed reduces "churning" in the aneurysmal cavity. Note that the first portion 62 and the second portion 64 can be separated only by pulling these portions apart and not by pushing these portions towards each other; this is so because the angled sides 72 are sloped relative to the longitudinal axis of the guide wire 22.

What is claimed is:

1. A bifurcated graft for reinforcing a branched vascular passageway, said graft having a main graft branch, a first graft branch, and a second branch, said passageway having a main passageway branch, a first passageway branch, and a second passageway branch, said graft comprising a tube having ends and a split between the first graft branch and the second graft branch, said first graft branch and second graft branch sharing a common longitudinal axis and being adapted such that one end of the graft is in contact with the first passageway branch and the opposite end of the graft is in contact with the second passageway branch upon complete deployment.

2. The graft as claimed in claim 1 wherein the graft has a middle portion having a larger outer diameter than that of the ends of the graft.

3. The graft, as claimed in claim 1 wherein the graft has a central diameter adjacent the split and wherein the length of the septum is approximately 18% longer than the central diameter.

* * * * *